United States Patent
Venkataramani

(10) Patent No.: US 9,486,146 B2
(45) Date of Patent: Nov. 8, 2016

(54) DETECTING TUMOROUS BREAST TISSUE IN A THERMAL IMAGE

(71) Applicant: Xerox Corporation, Norwalk, CT (US)

(72) Inventor: Krithika Venkataramani, Bangalore (IN)

(73) Assignee: Xerox Corporation, Norwalk, CT (US)

( * ) Notice: Subject to any disclaimer, the term of this patent is extended or adjusted under 35 U.S.C. 154(b) by 75 days.

(21) Appl. No.: 14/668,287

(22) Filed: Mar. 25, 2015

(65) Prior Publication Data
US 2016/0278641 A1  Sep. 29, 2016

(51) Int. Cl.
*G06K 9/00* (2006.01)
*A61B 5/01* (2006.01)
(Continued)

(52) U.S. Cl.
CPC ............ *A61B 5/015* (2013.01); *A61B 5/4312* (2013.01); *A61B 5/746* (2013.01); *G06T 7/0012* (2013.01);
(Continued)

(58) Field of Classification Search
USPC .................................................. 382/128–134
See application file for complete search history.

(56) References Cited

U.S. PATENT DOCUMENTS 6,757,412 B1  6/2004 Parsons et al.
7,181,056 B2  2/2007 Campanini et al.
(Continued)

FOREIGN PATENT DOCUMENTS

EP  1840833  10/2007

OTHER PUBLICATIONS

Mestha et al., "Processing a Video for Spatial and Temporal Magnification With Minimized Image Degradation", U.S. Appl. No. 13/708,125, filed Dec. 7, 2012.
(Continued)

*Primary Examiner* — Alex Liew
(74) *Attorney, Agent, or Firm* — Philip E. Blair; Fleit Gibbons Gutman Bongini & Bianco P.L.

(57) ABSTRACT

What is disclosed is a system and method for detecting cancerous tissue in breast tissue using a thermal image. In one embodiment, the present tumor detection method involves selecting a region of interest in the thermal image to be processed for breast cancer screening. Thereafter, a percentage of pixels $p_1$ in the selected region having a temperature $T_{pixel}^1$, where $T_1 \le T_{pixel}^1 \le T_2$, is determined. A percentage of pixels $p_2$ in the selected region having a temperature $T_{pixel}^2$, where $T_3 \le T_{pixel}^2$, is determined. A ratio $$p_3 = P_{edge} / P_{block}$$

is also determined, where $P_{edge}$ is a number of pixels around a border of a suspected tumor within the selected region, and $P_{block}$ is a number of pixels in a perimeter of the selected region. A decision fusion rule R, as more fully disclosed herein, is utilized to determine, based on these determination whether tissue within that region is cancerous, or non-cancerous, or is suspicious of being cancerous.

20 Claims, 10 Drawing Sheets

(51) Int. Cl.
*A61B 5/00* (2006.01)
*H04N 5/33* (2006.01)
*G06T 7/00* (2006.01)

(52) U.S. Cl.
CPC ....... *H04N 5/33* (2013.01); *G06T 2207/10048* (2013.01); *G06T 2207/10116* (2013.01); *G06T 2207/20104* (2013.01); *G06T 2207/30068* (2013.01); *G06T 2207/30096* (2013.01)

(56) References Cited

U.S. PATENT DOCUMENTS

| | | | | |
|---|---|---|---|---|
| 7,466,848 | B2* | 12/2008 | Metaxas | A61B 5/055 382/128 |
| 2004/0234113 | A1* | 11/2004 | Miga | G06T 7/0012 382/128 |
| 2007/0058845 | A1* | 3/2007 | Diakides | G06F 19/321 382/128 |
| 2008/0292164 | A1* | 11/2008 | Azar | A61B 5/0091 382/131 |
| 2009/0028405 | A1* | 1/2009 | Degani | A61B 6/481 382/131 |
| 2009/0135191 | A1* | 5/2009 | Azar | A61B 6/502 345/522 |
| 2009/0196480 | A1* | 8/2009 | Nields | G06T 7/0028 382/132 |
| 2010/0104513 | A1* | 4/2010 | Rittscher | G06T 7/0012 424/9.1 |
| 2010/0284592 | A1* | 11/2010 | Arnon | A61B 5/015 382/128 |
| 2011/0172514 | A1 | 7/2011 | Lee et al. | |
| 2011/0243409 | A1 | 10/2011 | Naimi et al. | |
| 2016/0135686 | A1* | 5/2016 | Gencer | A61B 5/0093 600/474 |

OTHER PUBLICATIONS

Schaefer et al., "Thermography Based Breast Cancer Analysis Using Statistical Features and Fuzzy Classifications", 2009, Pattern Recognition, 42 (6), pp. 1133-1137.

Kapoor et al., "Image Segmentation and Asymmetry Analysis of Breast Thermograms for Tumor Detection", International Journal of Computer Applications (0975-8887), vol. 50, No. 9, pp. 40-45, Jul. 2012.

Qi et al., "Detecting Breast Cancer from Infrared Images by Asymmetry Analysis", Proceeding of the 22nd Annual EMBS International Conference, Jul. 23-28, 2000, pp. 1227-1228.

Ur et al., "Thermography Based Breast Cancer Detection Using Texture Features and Support Vector Machine", J Med Syst., Oct. 19, 2010.

"No Touch Breastscan", http://notouchbreastscan.com, accessed Jan. 26, 2015.

Meditherm med2000 Iris, "Meditherm Interpretation and Reporting Software", http://www.meditherm.com/specifications_iris.htm, Jan. 29, 2013.

* cited by examiner

DETECTING TUMOROUS BREAST TISSUE IN A THERMAL IMAGE

CROSS REFERENCE TO RELATED APPLICATIONS

This patent application is related to concurrently filed and commonly owned U.S. patent application Ser. No. 14/668,178, entitled: "Software Interface Tool For Breast Cancer Screening", by Krithika Venkataramani et al., which is incorporated herein in its entirety by reference.

TECHNICAL FIELD

The present invention is specifically directed to a software interface tool for breast cancer screening and a method for detecting cancerous breast tissue in a thermal image of the breast.

BACKGROUND

Breast cancer incidence rates are relatively high in women. Nearly 1 in 8 women in the western world and nearly 1 in 11 women in India will have breast cancer. In the western world, it is the leading cancer in women. In India, for example, it is the second after cervical cancer. Early detection is key to survival as the mortality rates are high for advanced stages. Mammography is considered the gold standard for breast cancer screening. Screening for breast cancers are commonly done via manual detection of a lump in the breast tissue and/or by an in-office mammography exam followed by human interpretation of the image created during the examination. In the mammography exam, the subject is subject to highly personal physical contact and a procedure which many subjects find discomforting. In subjects with dense breast tissue, the exam may not be as effective in spotting malignancies as for other subjects. Moreover, the equipment required for mammography is relatively large and relatively expensive. Since mammography is an x-ray machine it cannot be used at homes without supervision. The x-ray radiation itself may result in cancer. It is also not effective for younger women due to the dense breast tissue. There is also some evidence that the physical manipulation of the breast tissue during mammography could rupture the malignant cysts, thereby increasing risk of spreading the malignant cells to other tissues and into the subject's blood stream.

Thermography is an emerging alternative non-invasive and non-contact screening method for breast cancer detection. Thermal imaging captures the infra-red emissivity from the human body in the 7-10 μm wavelength range. Thermal imaging devices are useful for the detection of thermal activity in breast tissue due to a tumor's growth being enabled by causing new blood vessels to grow disproportionately through angiogenesis in the area of the tumor relative to surrounding tissue. This increased biophysical activity beneath the skin surface associated with tumor growth results in a higher metabolic rate which, in turn, results in an elevated temperature in that tissue. This appears as a hotspot in a thermal image containing that tissue. Recently, interest has been rekindled in thermography as a breast cancer screening approach with the improvement in thermal camera resolution and technology.

Trained radiologists and thermographers look for these abnormalities in thermal images to make a determination whether tissue is cancerous or is suspicious of being cancerous. If so, the subject may need to undergo additional tests, such as sonomammography followed by cancer diagnosis through histopathology by fine needle aspiration cytology or tissue biopsy. Thermographers and radiologists are increasingly demanding more powerful visualization software interface tools to assist them. Moreover, since medical practitioners trained in thermography are not readily available in rural areas in emerging markets like India, automatic screening tools will help open up these market for software applications for breast cancer screening and detection.

Accordingly, what is needed in this art are increasingly software tools which enable subjects as well as medical practitioners to manually or automatically analyze a thermal image of an area of breast tissue for the presence of cancerous tissue.

BRIEF SUMMARY

What is disclosed is a software interface tool for breast cancer screening that is designed for medical professionals to view and analyze suspicious regions for hot spots and hence facilitate a determination of whether identified areas of breast tissue are cancerous. Isotherm maps are constructed at designated temperature resolution. Maps are displayed on the screen. Point & click on the isotherm map can extract temperature values of pixels within the region covered by the isotherm contours. Also provided are isothermic views at different viewing angles which is advantageous for visual detection. Additional functionalities for hotspot selection, cropping, zooming, viewing at different angles, etc. are also enable by the present software interface. The present software interface further utilizes a tumor detection method which is also disclosed herein. In one embodiment, the present tumor detection method involves selecting a region of interest in the thermal image to be processed for breast cancer screening. Thereafter, a percentage of pixels $p_1$ in the selected region having a temperature $T_{pixel}^1$, where $T_1 \leq T_{pixel}^1 \leq T_2$, is determined. A percentage of pixels $p_2$ in the selected region having a temperature $T_{pixel}^2$, where $T_3 \leq T_{pixel}^2$, is determined. A ratio $$p_3 = P_{edge} / P_{block}$$

is also determined, where $P_{edge}$ is a number of pixels around a border of a suspected tumor within the selected region, and $P_{block}$ is a number of pixels in the perimeter of the selected region. In a manner more fully disclosed herein, a decision fusion rule R is then utilized to determine whether tissue within that region is cancerous, non-cancerous, or is suspicious of being cancerous.

Features and advantages of the above-described software interface tool and tumor detection method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a software interface tool for breast cancer screening and a method for detecting cancerous tissue in a thermal image of a breast.

NON-LIMITING DEFINITIONS

Figure 1:
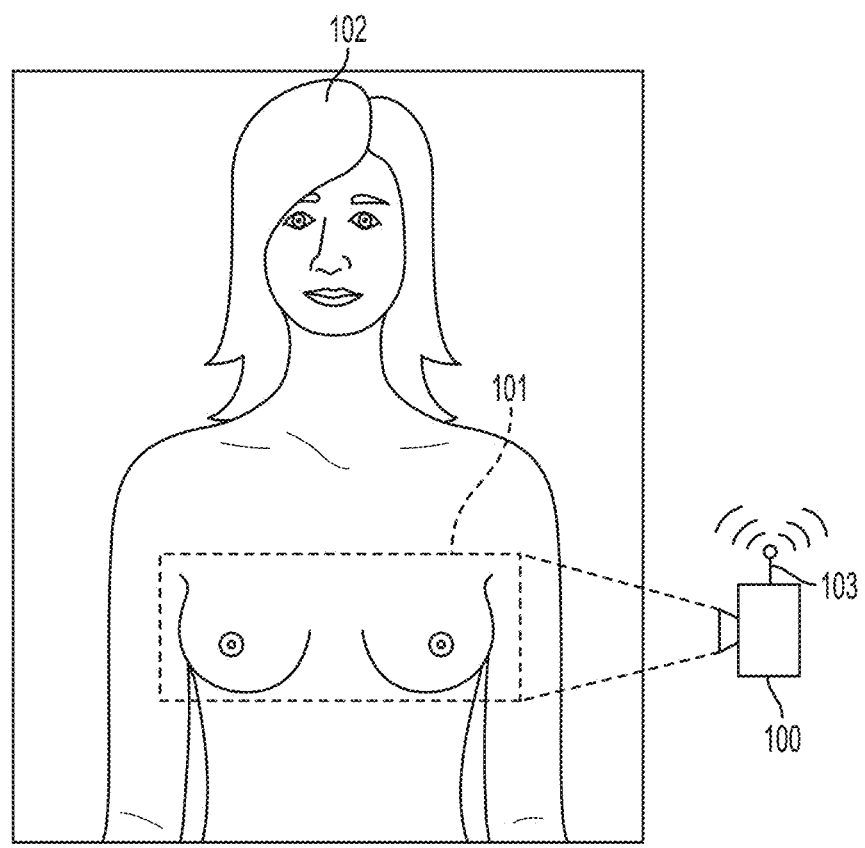
FIG. 1 shows an example thermal imaging system capturing a thermal image of an area of the breast of a female subject.

A "subject" refers to a living being. Although the term "person" or "patient" may be used throughout this disclosure, it should be appreciated that the subject may be something other than a human such as, for example, a primate. Therefore, the use of such terms is not to be viewed as limiting the scope of the appended claims strictly to humans. FIG. 1 shows an example human female patent 102.

A "thermal imaging system" is a camera with a lens that focuses infrared energy from objects in a scene onto an array of specialized sensors which convert infrared energy into electrical signals on a per-pixel basis and outputs a thermal image comprising an array of pixels with color values corresponding to surface temperatures of the objects in the image across a thermal wavelength band. FIG. 1 shows a thermal imaging system 100 capturing a thermal image 101 of a female subject 102 which, in turn, is communicated to a workstation via a wireless transmissive element 103, shown as an antenna. Although the subject in FIG. 1 is female, the subject/subject may be male. The thermal imaging system can be any of: a single-band infrared camera, a multi-band infrared camera in the thermal range, and a hyperspectral infrared camera in the thermal range. Specialized processors inside the thermal camera associate pixel color values with different temperatures and provide output color values of each pixel in the resulting thermal image. The resolution for a thermal camera is effectively the size of the pixel. Smaller pixels mean that more pixels will go into the image for the same region of interest giving the resulting image higher resolution and thus better spatial definition. Because the amount of black-body radiation emitted by an object increases with the object's temperature, variations in temperatures of objects are observable in a thermal image. Thermal cameras generally consist of five primary components: 1) optics comprising specialized focal plane arrays (FPAs) that respond to defined wavelengths of the infrared range of the electromagnetic (EM) spectrum ($\approx 7.5$ to $\approx 14$ µm); 2) a detector for detecting radiation in the infrared range; 3) an amplifier for amplifying the received radiation; 4) a display for viewing the captured images; and 5) signal processing hardware such as: a CPU, memory, storage, for performing mathematical algorithms which interpret data and construct an IR image. Common thermal imaging systems include: InSb, InGaAs, HgCdTe, and QWIP FPA. Newer technologies utilize an uncooled Microbolometer as FPA sensors. Thermal cameras offer a relatively large dynamic range of temperature settings. However, for the purposes hereof, it is preferable that the camera's temperature range be relatively small centered around subject's body surface temperature so that small temperature variations are amplified in terms of pixel color changes to provide a better measure of temperature variation. The reader is directed to any of a variety of texts on thermal imaging including: "*Infrared Thermal Imaging: Fundamentals, Research and Applications*", Michael Vollmer, Klaus Peter Möllmann, Wiley-VCH; 1$^{st}$ Ed. (2010) ISBN-13: 978-3527407170, which is incorporated herein in its entirety by reference. A method for enhancing a spatial resolution of a thermal image or a portion thereof, is disclosed in: "Processing A Video For Spatial And Temporal Magnification With Minimized Image Degradation", U.S. patent application Ser. No. 13/708,125, by Mestha et al., which is incorporated herein in its entirety by reference. Thermal cameras are readily available in various streams of commerce. Thermal images are captured using a thermal imaging system.

A "thermal image" is an image captured using a thermal camera. Each thermal image comprises a plurality of pixels with each pixel having an associated corresponding temperature value. A thermal image of a subject's breasts is shown in the visualization screen 201 of FIG. 2. The thermal images are received by the workstation for manipulation by various aspects of the functionality of the software interface disclosed herein. Although the thermal images herein are shown in black/white, it should be appreciated that thermal images are in color.

"Receiving a thermal image" is intended to be widely construed and includes: retrieving, receiving, capturing, acquiring, or otherwise obtaining a thermal image or a video comprising a plurality of thermal images for processing in accordance with the methods disclosed herein. Thermal images can be retrieved from a memory or storage device of the thermal imaging device, or obtained from a remote device over a network. Thermal images may be retrieved from a media such as a CDROM or DVD. Thermal images may be downloaded from a web-based system which makes such images available for processing. Thermal images can also be retrieved using an application such as those which are widely available for handheld cellular devices and processed on the user's cellphone or other handheld computing device such as an iPad or tablet. Thermal images are of a breast area of a subject.

A "breast area of the subject" encompasses tissue of the breast itself and may further include portions of surrounding non-breast tissue as are needed for breast cancer screening and detection. Regions of breast tissue are automatically or manually identified in the thermal image for analysis.

Figure 2:
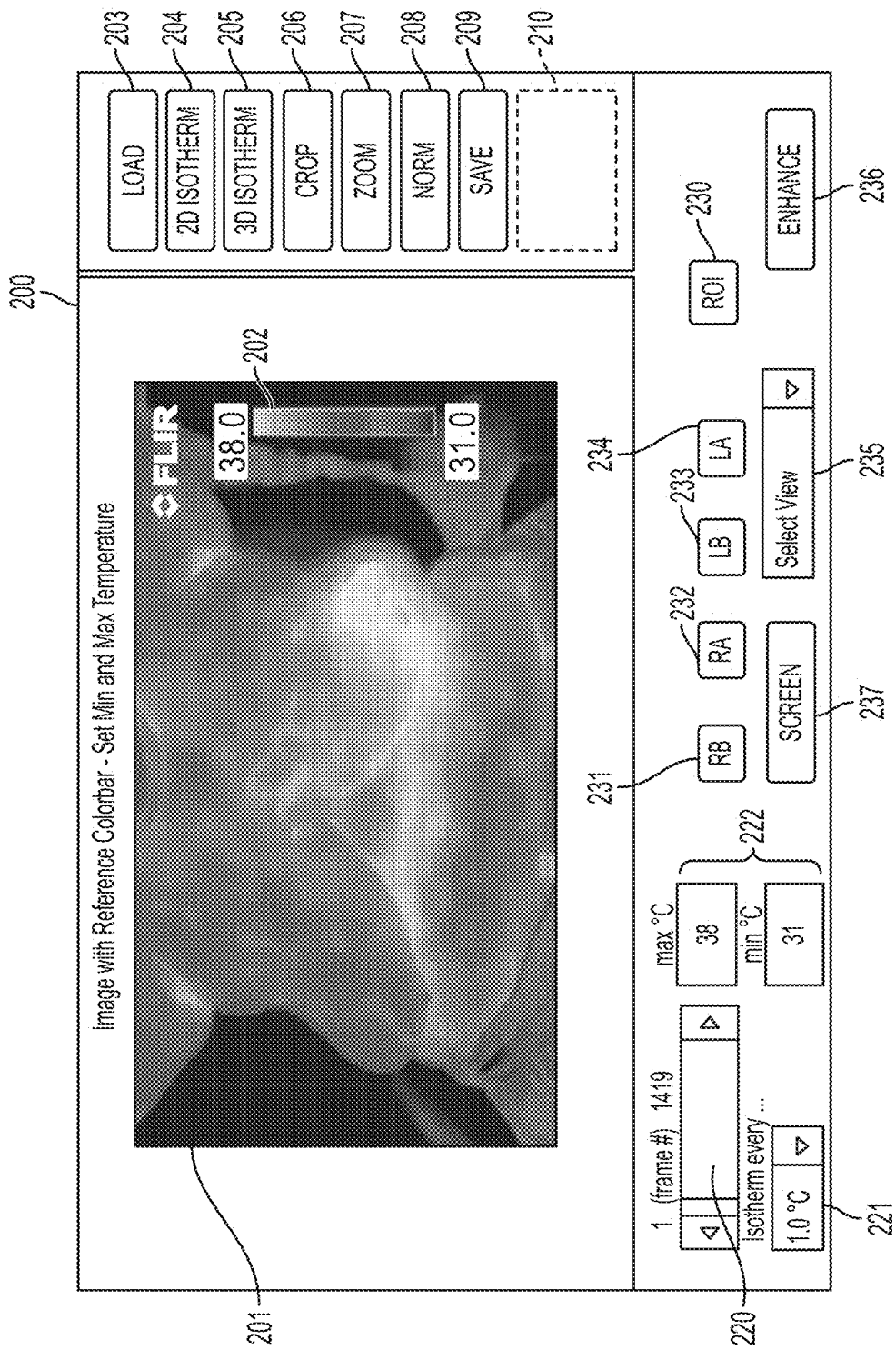
FIG. 2 shows one example embodiment of the software interface tool disclosed herein.

A "software interface tool" is a composite of user-selectable functionality displayed on a display device such as a touchscreen display of a computer workstation. FIG. 2 shows one example embodiment of the present software interface tool 200. Various embodiments of the present software interface tool comprise a visualization screen, a temperature bar, and a plurality of selectable software objects.

A "VISUALIZATION SCREEN" refers to a portion of the software interface tool (shown at 201) wherein at least one thermal image of at least one breast of a subject is displayed.

A "TEMPERATURE BAR" refers to a portion of the present software interface tool (shown at 202) wherein temperature values which are associated with the various colors comprising the displayed thermal image are shown.

A "selectable software object" refers to a graphical widget which can take a variety of forms such as, for instance, a button, a pull-down menu, a slidable bar, and the like, as are commonly known and widely understood in the software arts. Specialized machine readable/executable program instructions associated with a particular "button" is designed to perform functionality represented by that particular widget. Once selected by a user clicking a mouse thereon or manually touching that particular button on a touch-sensitive display device, causes a central processor unit (CPU) to retrieve those program instructions from memory and execute those instructions.

The "LOAD" object (shown at 203) is a widget which, when selected, effectuates a display of an infrared image on the visualization screen 201. Pixels in the image having a highest temperature value are displayed in first color and pixels having a lowest temperature are displayed in second color. Pixels with temperature values between the lowest and highest temperatures are displayed in gradations of color between the first and second colors. Temperature values associated with the displayed colors appear on the temperature bar 202.

A "2D ISOTHERM" object 204 is a widget which, when selected, effectuates a 2D display of contour lines on the visualization screen 201. The contour lines circumscribe or "bound" various groups of colored pixels in the image which have substantially similar temperature values.

A "3D ISOTHERM" object 205 is a widget which, when selected, effectuates a 3D display of contour lines on the visualization screen 201 wherein an increasing height of the contour lines is associated with an increase in temperature values of pixels in the displayed thermal image.

A "CROPPING" object 206 enables a user to selectively crop any portion of the displayed thermal image.

A "ZOOMING" object 207 enables a user to enlarge any portion of the displayed image. In one embodiment, zooming is performed using an embodiment of the image enhancement method disclosed in U.S. patent application Ser. No. 13/708,125 entitled: "Processing A Video For Spatial And Temporal Magnification With Minimized Image Degradation", by Mestha et al. (Allowed 11-25-2014).

A "NORMALIZATION" object 208 normalizes temperatures within an identified region of interest to a highest temperature or, alternatively, to a lowest temperature value.

A "SAVE" object 209 enables the user to save any portion of the displayed image to a memory or storage device.

A "TEXT AREA" at 210 wherein messages are displayed for the user such as, for example, a message indicating a probability that the tissue in the identified region of interest can be categorized as being any of thermal BIRADs category, thermos-biological category, non-cancerous category, suspicious of being cancerous category, and cancerous category.

A "FRAME SLIDER" object 220 enables a user to move forward and backward within a video such that a different image frame is displayed on the visualization screen.

An "ISOTHERM GRADATION" object 221 effectuates the selection of a temperature gradation for the displayed contour lines.

A "GRADATION" object 222 effectuates the selection of a temperature gradation for the displayed contour lines.

Figure 3:
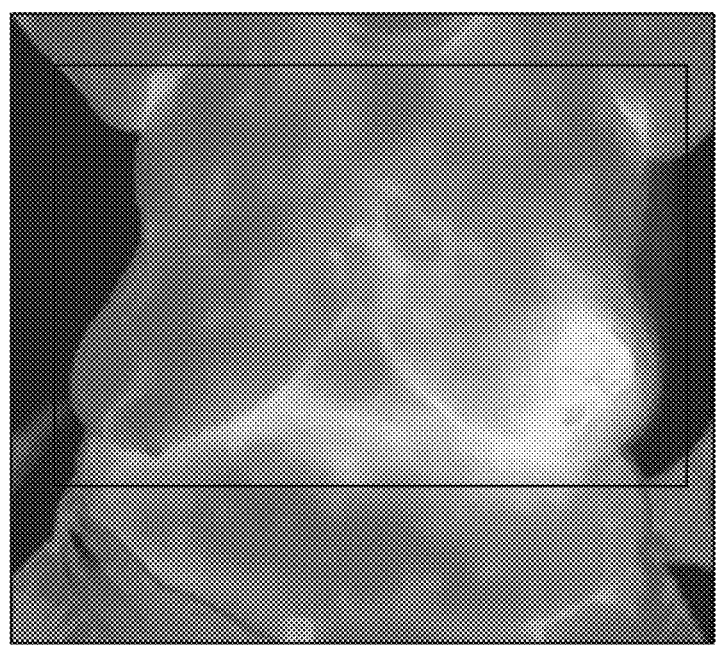
FIG. 3 shows one example selected region of interest substantially comprising the right and left breasts of the subject in the image of FIG. 2.
Figure 4:
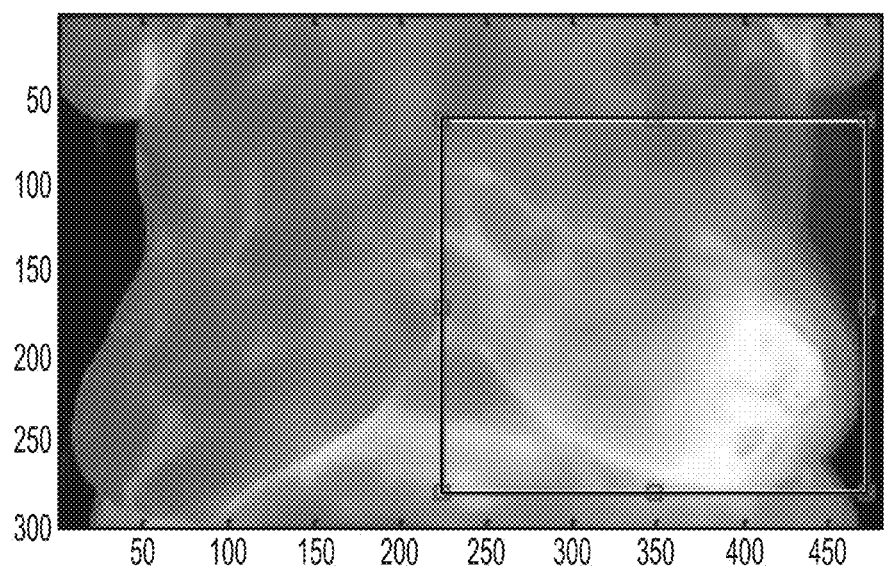
FIG. 4 shows the subject's left breast having been selected as a region of interest.
Figure 5:
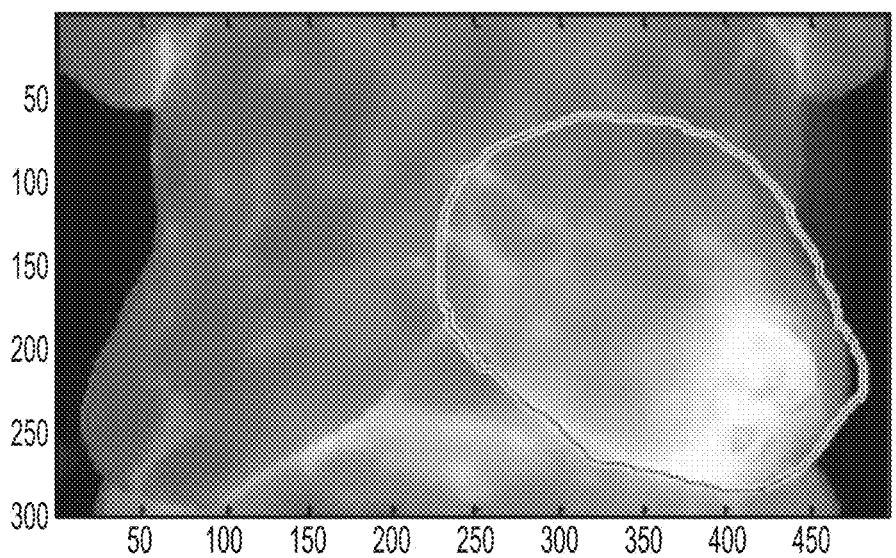
FIG. 5 shows a region of interest substantially comprising the subject's left breast having been manually selected by a user.
Figure 6:
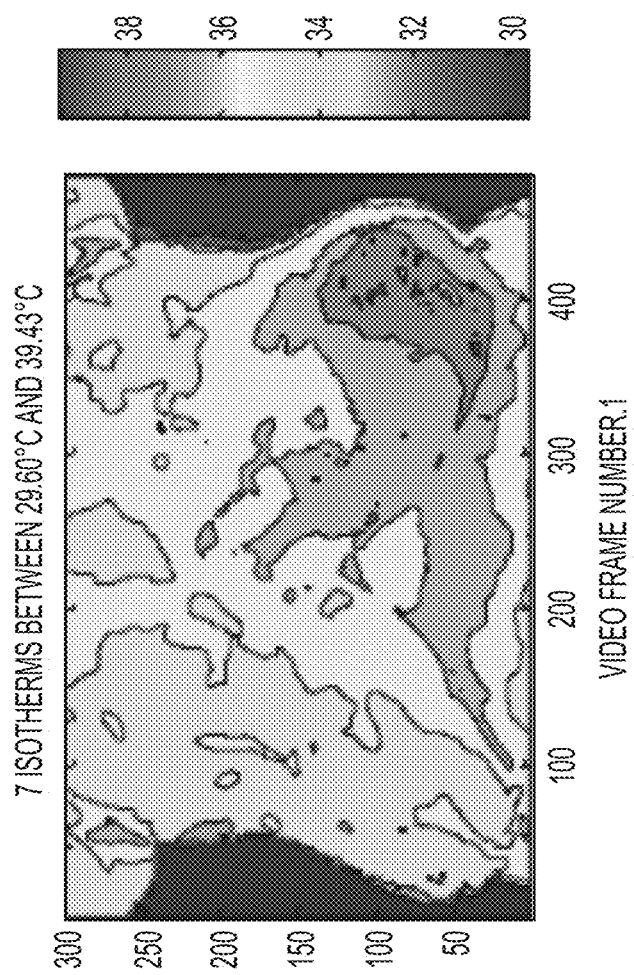
FIG. 6 shows example displayed 2D contour lines of the regions of interest of FIG. 3.
Figure 7:
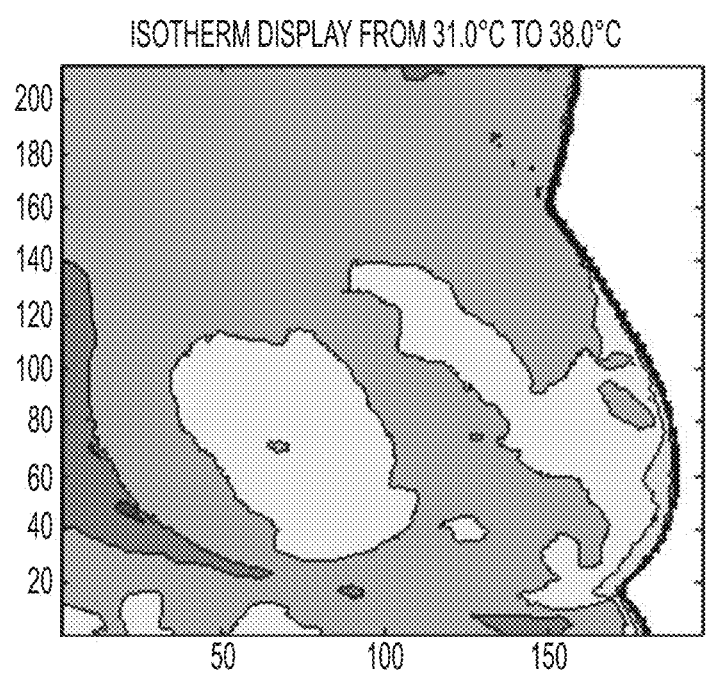
FIG. 7 shows example displayed 2D contour lines of the regions of interest of FIG. 5.

A "REGION OF INTEREST (ROI)" object 230 enables either the manual or automatic selection of at least one region of interest in the displayed thermal image. A region of interest can be identified in a thermal image using any of a wide array of image processing techniques which include, for example, object identification, pattern recognition, pixel classification, color, texture, spatial relationships, and/or spatial features. A region of interest can be manually identified using, for instance, a mouse to draw a rubber-band box around a region of interest. One example region of interest, which substantially comprises the right and left breasts of the subject, is shown at 300 in FIG. 3. FIG. 4 shows the subject's left breast having been selected as a region of interest. FIG. 5 shows a region of interest substantially comprising the subject's left breast having been manually selected by a user. Example displayed 2D contour lines of the regions of interest of FIG. 3 are shown in FIG. 6. Example displayed 2D contour lines of the regions of interest of FIG. 5 are shown in FIG. 7. It should be appreciated that, in the absence of a selection of a region of interest, the entire thermal image becomes the region of interest by default.

A "RIGHT BREAST (RB)" object 231 enables the automatic identification of the right breast in the displayed image.

A "LEFT BREAST (LB)" object 232 enables the automatic identification and segmentation of the left breast in the displayed image.

A "RIGHT AXILLA (RA)" object 233 and a "LEFT AXILLA (LA)" object 234 effectuate automatic selection of a right and left regions of interest; specifically adjacent tissues containing lymph nodes.

A "VIEW ANGLE" object 235 enables a user to change a view angle of the displayed thermal image.

Figure 8:
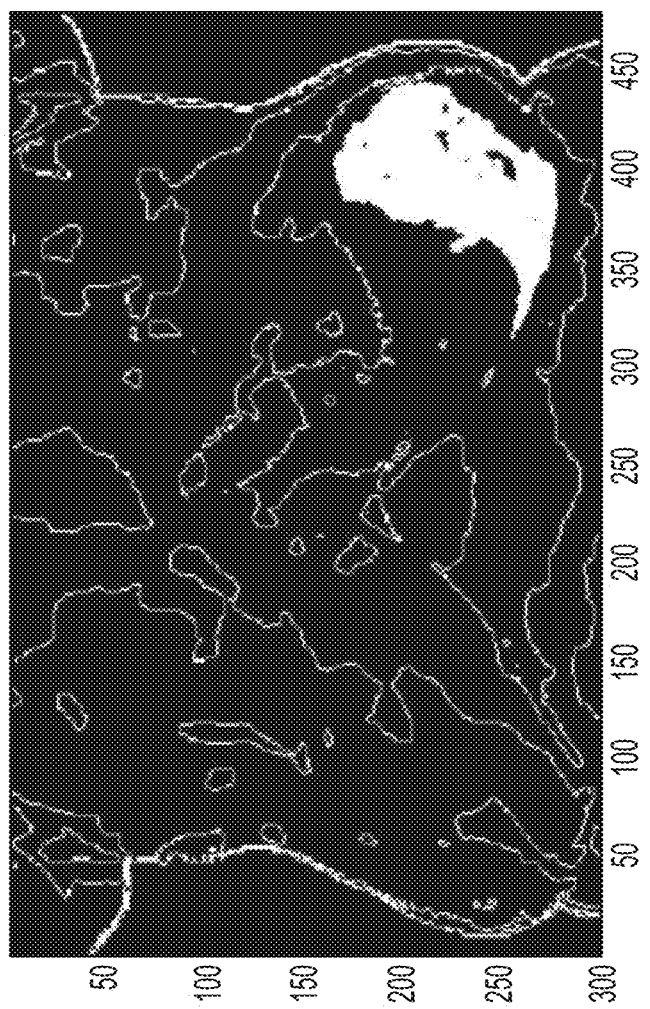
FIG. 8 shows an area of the subject's left breast in the contour image of FIG. 6 having been visually enhanced.

A "VISUAL ENHANCEMENT" object 236 enables a region of tissue to be visually enhanced by being displayed prominently in the displayed thermal image by subduing surrounding tissue. FIG. 8 shows an area of the subject's left breast in the contour image of FIG. 6 having been visually enhanced by highlighting the desired area and subduing areas outside that area.

A "SCREENING" object 237 effectuates the manual or automatic screening of the breast tissue in the identified region of interest for the presence of cancerous tissue, the absence of cancerous tissue, or the suspicion of cancerous tissue. In one embodiment, specialized machine readable/executable program instructions associated with the screening object effectuates a detection protocol which includes any combination of: a histogram distance method, fractal dimensions, texture based, deep learning, machine learning, neural network, bio heat-based, frequency domain based, 2D and 3D.

It should be appreciated that the steps of "determining", "analyzing", "identifying", "receiving", "processing", "selecting", "performing" and the like, as used herein, include the application of various signal processing and mathematical operations applied to data and signals, according to any specific context or for any specific purpose. It should be appreciated that such steps may be facilitated or otherwise effectuated by a microprocessor executing machine readable program instructions retrieved from a memory or storage device.

Flow Chart of Tumor Detection

Figure 9:
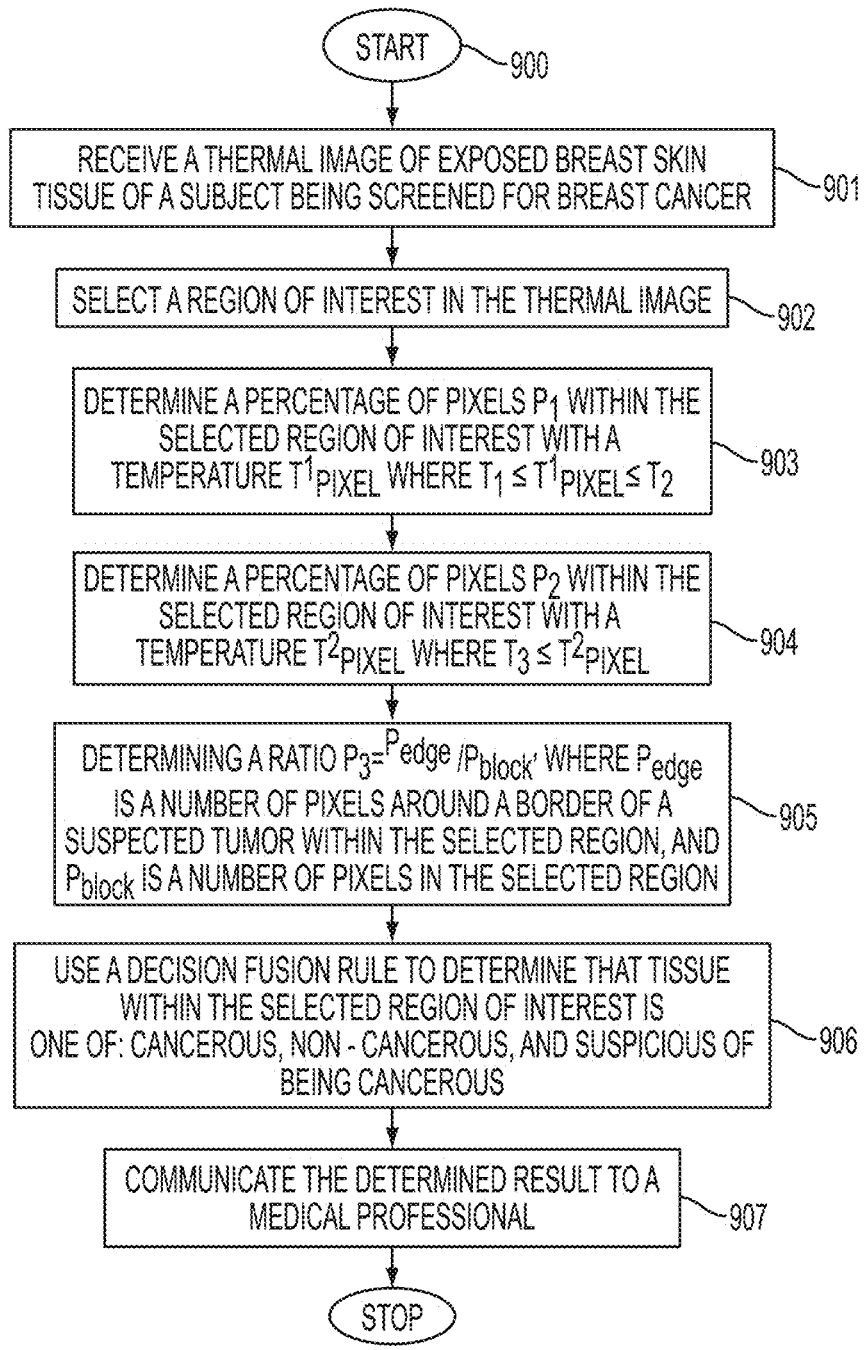
FIG. 9 is a flow diagram which illustrates one example embodiment of a method for detecting tumorous breast tissue using a thermal image.

Reference is now being made to the flow diagram of FIG. 9 which illustrates one example embodiment of a method for detecting tumorous breast tissue using a thermal image. Flow processing starts at steps 900 and immediately proceeds to step 901.

At step 901, receive a thermal image of exposed breast skin tissue of a subject being screened for breast cancer. The thermal image has been captured by a thermal imaging system. The received thermal image can be displayed on the visualization interface by a user having selected the LOAD object 203 of the software interface tool of FIG. 2. One example thermal imaging system is shown and discussed with respect to the example embodiment of FIG. 1. Example thermal images are shown in FIGS. 2-8.

At step 902, select a region of interest (ROI) in the thermal image. Example selected regions of interest are shown in FIGS. 3-5. A region of interest can be manually or automatically selected by a user selection of the ROI object 230 of the software interface tool of FIG. 2. The following functionality would be implemented in response to a user having selected the SCREENING object 237 of the software interface tool of FIG. 2.

At step 903, determine a percentage of pixels $p_1$ within the selected region of interest which have a temperature $T_{pixel}^1$ such that $T_1 \leq T_{pixel}^1 \leq T_2$. In this embodiment, $T_1 = T_{max}$, where $T_{max}$ is a maximum temperature of the subject, and $T_2 = \lfloor T_1 \rfloor - 1°$ C.

At step 904, determine a percentage of pixels $p_2$ within the selected ROI with a second temperature $T_{pixel}^2$ such that $T_3 \leq T_{pixel}^2$. In this embodiment, $T_3 = T_{avg} + (T_{max} - T_{avg})/3$, where $T_{avg}$ is an average temperature of the subject.

At step 905, determining a ratio $$p_3 = P_{edge} / P_{block},$$

where $P_{edge}$ is a number of pixels around a border of a suspected tumor within the selected region, and $P_{block}$ is a number of pixels in the perimeter of the selected region.

At step 906, using a decision fusion rule R to determine that tissue within the selected region of interest is one of: cancerous, non-cancerous, or suspicious of being cancerous.

At step 907, communicate the determined result to a medical professional. The determination may also be communicated to a memory, a storage device, a display device, a handheld wireless device, a handheld cellular device, and/or a remote device over a network. Thereafter, in this embodiment, further processing stops.

It should also be appreciated that the flow diagrams depicted herein are illustrative. One or more of the operations may be performed in a differing order. Other operations may be added, modified, enhanced, or consolidated. Variations thereof are intended to fall within the scope of the appended claims.

Example Special Purpose Computer

Figure 10:
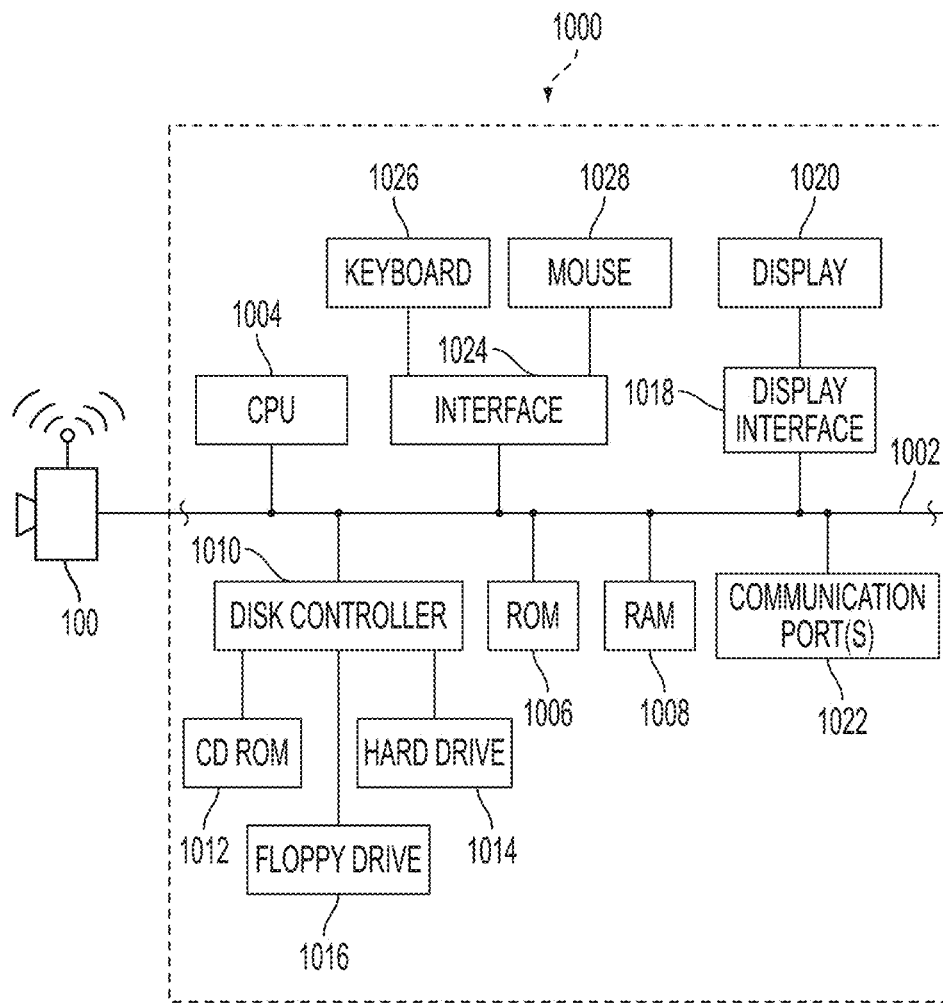
FIG. 10 illustrates one embodiment of a functional block diagram of a special purpose computer system for implementing various aspect of the present software interface tool of FIG. 2 and the tumor detection method shown and described with respect to the flow diagram of FIG. 9.

Reference is now being made to FIG. 10 which is a functional block diagram of a special purpose computer system 1000 for implementing various aspect of the present software interface tool of FIG. 2 and the tumor detection method shown and described with respect to the flow diagram of FIG. 9. Such a special purpose processor is capable of executing machine executable program instructions and may comprise any of a micro-processor, microcontroller, ASIC, electronic circuit, or any combination thereof.

In FIG. 10, communications bus 1002 is in communication with a central processing unit (CPU) 1004 capable of executing machine readable program instructions for performing any of the calculations, comparisons, logical operations, and other program instructions for performing any of the steps described above with respect to the flow diagrams and illustrated embodiments hereof. Processor 1004 is in communication with memory (ROM) 1006 and memory (RAM) 1008 which, collectively, constitute example storage devices. Such memory may be used to store machine readable program instructions and other program data and results to sufficient to carry out any of the functionality described herein. Disk controller 1010 interfaces with one or more storage devices 1014 which may comprise external memory, zip drives, flash memory, USB drives, or other devices such as CD-ROM drive 1012 and floppy drive 1016. Storage device stores machine executable program instructions for executing the methods hereof. Such storage devices may be used to implement a database wherein various records are stored. Display interface 1018 effectuates the display of information on display 1020 in various formats such as, for instance, audio, graphic, text, and the like. Interface 1024 effectuates a communication via keyboard 1026 and mouse 1028, collectively a graphical user interface. Such a graphical user interface is useful for a user to enter information about any of the displayed information in accordance with various embodiments hereof. Communication with external devices may occur using example communication port(s) 1022. Such ports may be placed in communication with any of the example networks shown and described herein, such as the Internet or an intranet, either by direct (wired) link or wireless link. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. The teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system and other specialized programs such Windows or Java.

One or more aspects of the teaching disclosed herein are intended to be incorporated in an article of manufacture, including one or more computer program products, having computer usable or machine readable media. The article of manufacture may be included on at least one storage device readable by a machine architecture embodying executable program instructions capable of performing the methods described herein. The article of manufacture may be shipped, sold, leased, or otherwise provided separately either alone or as part of an add-on, update, upgrade, or product suite.

It will be appreciated that the above-disclosed and other features and functionality, or alternatives thereof, may be desirably combined into many other different systems or applications. As such, various presently unforeseen or unanticipated alternatives, modifications, variations, or improvements therein may become apparent and/or subsequently made by those skilled in the art which are also intended to be encompassed by the following claims. Accordingly, the embodiments set forth above are illustrative and not limiting. Changes to the above-described embodiments may be made without departing from the spirit and scope of the invention.

The teachings of any printed publications including patents and patent applications, are each separately hereby incorporated by reference in their entirety.

What is claimed is:

1. A method for detecting tumorous breast tissue using a thermal image, the method comprising:
   receiving a thermal image of breast skin tissue of a subject being screened for breast cancer, said thermal image having been captured by a thermal imaging system and comprising a plurality of pixels each having a corresponding temperature value;
   selecting at least one region of interest in said thermal image;
   determining a percentage of pixels $p_1$ in said selected region with a temperature $T_{pixel}^1$, where $T_1 \le T_{pixel}^1 \le T_2$;
   determining a ratio
   $$p_3 = P_{edge} / P_{block},$$
   where $P_{edge}$ is a number of pixels around a border of a suspected tumor within said selected region, and $P_{block}$ is a number of pixels in a perimeter of said selected region; and
   using a decision fusion rule R to determine that tissue in said region of interest is one of: cancerous, non-cancerous, or suspicious of being cancerous.

2. The method of claim 1, wherein said thermal imaging system is any of: a single-band infrared camera, a multi-band infrared camera in the thermal range, and a hyperspectral infrared camera in the thermal range.

3. The method of claim 1, wherein said decision fusion rule R is based on any combination of: $R_1, R_2, R_3$, where: $R_1 = (p_1 \ge Threshold_1)$, $R_2 = (p_2 \ge Threshold_2)$, and $R_3 = (p_3 \ge Threshold_3)$.

4. The method of claim 3, wherein $Threshold_1$, $Threshold_2$, $Threshold_3$ comprise user-defined threshold values based on any combination of: tumor characteristics, subject age, race, sex, and medical history.

5. The method of claim 3, where said decision fusion rule, R, comprises any of: a majority rule of $(R_1, R_2, R_3)$, and a weighted sum of $(R_1, R_2, R_3)$.

6. The method of claim 1, wherein $T_1 = T_{max}$, where $T_{max}$ is a maximum temperature of said subject, and $T_2 = \lfloor T_1 \rfloor - 1°$ C.

7. The method of claim 1, wherein $T_3 = T_{avg} + (T_{max} - T_{avg})/3$, where $T_{max}$ is a maximum temperature of said subject, and $T_{avg}$ is an average temperature of said subject.

8. The method of claim 1, wherein, in response to having performed screening, displaying a message indicating a probability that tissue in said region of interest can be categorized as being in any category of: thermal BIRADs category, thermo-biological category, non-cancerous category, suspicious of being cancerous category, and cancerous category.

9. The method of claim 1, further comprising communicating any of said determinations to any of: a medical staff, a medical data repository, a memory, a storage device, a display device, a handheld wireless device, a handheld cellular device, and a remote device over a network.

10. The method of claim 1, wherein, in response to a determination that tissue in said selected region is cancerous, performing any of: initiating an alert, and signaling a medical professional.

11. A system for detecting tumorous breast tissue using a thermal image, the system comprising:
   a memory and a storage device; and
   a microprocessor in communication with said memory and storage device, said microprocessor executing machine readable program instructions for performing:
      receiving a thermal image of breast skin tissue of a subject being screened for breast cancer, said thermal image having been captured by a thermal imaging system and comprising a plurality of pixels each having a corresponding temperature value;
      selecting at least one region of interest in said thermal image;
      determining a percentage of pixels $p_1$ in said selected region having a first temperature $T_{pixel}^1$, where $T_1 \le T_{pixel}^1 \le T_2$;
      determining a ratio
      $$p_3 = P_{edge} / P_{block},$$
      where $P_{edge}$ is a number of pixels around a border of a suspected tumor within said selected region, and $P_{block}$ is a number of pixels in a perimeter of said selected region; and
      using a selected decision fusion rule, R, to determine that tissue within said region of interest is one of: cancerous, non-cancerous, or suspicious of being cancerous.

12. The system of claim 11, wherein said thermal imaging system is any of: a single-band infrared camera, a multi-band infrared camera in the thermal range, and a hyperspectral infrared camera in the thermal range.

13. The system of claim 11, wherein said decision fusion rule R is based on any combination of: $R_1, R_2, R_3$, where: $R_1 = (p_1 \ge Threshold_1)$, $R_2 = (p_2 \ge Threshold_2)$, and $R_3 = (p_3 \ge Threshold_3)$.

14. The system of claim 13, wherein $Threshold_1$, $Threshold_2$, $Threshold_3$ comprise user-defined threshold values based on any combination of: tumor characteristics, subject age, race, sex, and medical history.

15. The system of claim 13, where said decision fusion rule, R, comprises any of: a majority rule of $(R_1, R_2, R_3)$, and a weighted sum of $(R_1, R_2, R_3)$.

16. The system of claim 11, wherein $T_1 = T_{max}$, where $T_{max}$ is a maximum temperature of said subject, and $T_2 = \lfloor T_1 \rfloor - 1°$ C.

17. The system of claim 11, wherein $T_3 = T_{avg} + (T_{max} - T_{avg})/3$, where $T_{max}$ is a maximum temperature of said subject, and $T_{avg}$ is an average temperature of said subject.

18. The system of claim 11, wherein, in response to having performed screening, displaying a message indicating a probability that tissue in said region of interest can be categorized as being in any category of: thermal BIRADs category, thermo-biological category, non-cancerous category, suspicious of being cancerous category, and cancerous category.

19. The system of claim 11, further comprising communicating any of said determinations to any of: a medical staff, a medical data repository, a memory, a storage device, a display device, a handheld wireless device, a handheld cellular device, and a remote device over a network.

20. The system of claim 11, wherein, in response to a determination that tissue in said selected region is cancerous, performing any of: initiating an alert, and signaling a medical professional.

\* \* \* \* \*